United States Patent
Tokizawa et al.

(10) Patent No.: US 6,528,500 B1
(45) Date of Patent: Mar. 4, 2003

(54) AZOLE DERIVATIVES OR SALTS THEREOF

(75) Inventors: Minoru Tokizawa, Narita (JP); Hiromichi Eto, Narita (JP); Kazuya Ishida, Narita (JP); Kazunori Maebashi, Narashino (JP); Masaru Matsumoto, Chiba (JP); Takemitsu Asaoka, Narita (JP); Susumu Sato, Narita (JP)

(73) Assignee: SSP Co., Ltd., Tokyo (JP)

( * ) Notice: Subject to any disclaimer, the term of this patent is extended or adjusted under 35 U.S.C. 154(b) by 0 days.

(21) Appl. No.: 09/671,013

(22) Filed: Sep. 28, 2000

(30) Foreign Application Priority Data

Sep. 29, 1999 (JP) ............................................. 11-276431

(51) Int. Cl.[7] ..................... C07F 9/6518; A61K 31/675
(52) U.S. Cl. ......................... 514/93; 514/383; 548/112; 548/268.6
(58) Field of Search ............................... 548/268.6, 112; 514/383, 93

(56) References Cited

U.S. PATENT DOCUMENTS

| | | |
|---|---|---|
| 5,147,886 A | 9/1992 | Tokizawa et al. |
| 5,939,448 A | 8/1999 | Tokizawa et al. |
| 5,945,438 A | 8/1999 | Tokizawa et al. |
| 5,986,144 A | 11/1999 | Tokizawa et al. |
| 6,002,028 A | 12/1999 | Tokizawa et al. |
| 6,008,239 A | 12/1999 | Kaneko et al. |
| 6,040,325 A | 3/2000 | Takeda et al. |
| 6,083,968 A | 7/2000 | Takeda et al. |

FOREIGN PATENT DOCUMENTS

| | | |
|---|---|---|
| EP | 0 927 719 | 7/1999 |
| EP | 1 040 828 | 10/2000 |
| WO | WO 93/11118 | 6/1993 |
| WO | WO 97/28169 | 8/1997 |
| WO | WO 99/33464 | 7/1999 |

*Primary Examiner*—Patricia L. Morris

(57) ABSTRACT

Described is an azole derivative represented by the following formula (1):

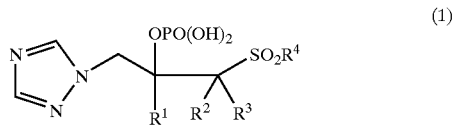

wherein, $R^1$ represents a substituted phenyl group, $R^2$ and $R^3$ each represents a fluorine atom, an alkyl group or the like, and $R^4$ represents an alkyl group, or salt thereof; and a medicament comprising the derivative or salt as an effective ingredient.

The compound according to the present invention exhibits excellent antimycotic action and has good aqueous solubility.

9 Claims, No Drawings

AZOLE DERIVATIVES OR SALTS THEREOF

BACKGROUND OF THE INVENTION

1. Field of the Invention

The present invention relates to azole derivatives and salts thereof each having excellent antimycotic action and good aqueous solubility, and medicaments containing the derivatives or salts as an effective ingredient, respectively.

2. Description of the Related Art

A number of azole compounds having antimycotic action have already been known. Although the conventional azole compounds can be used as a dermatologic preparation for external use, their low solubility in an aqueous solvent disturbs formulation of them into an aqueous preparation such as orally administrable preparation or intravenously administrable preparation without any treatment.

It is therefore proposed to add a complex forming agent or a cyclodextrin derivative in order to obtain an aqueous preparation (European Patent Application Laid-Open No. 0440372).

Use of such an additive is however not preferred for suppressing the side effect to the minimum level and to make the azole derivative itself soluble in an aqueous solvent is desired.

SUMMARY OF THE INVENTION

An object of the present invention is therefore to provide a novel compound having both strong antimycotic action and excellent solubility in an aqueous solvent.

With the foregoing in view, the present inventors have synthesized a variety of novel azole derivatives and carried out an extensive investigation on their antimycotic action and solubility in an aqueous solvent. As a result, it has been found that the compounds represented by the below-described formula (1) satisfy both, leading to the completion of the present invention.

In one aspect of the present invention, there is thus provided an azole derivative represented by the following formula (1):

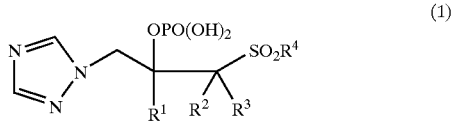

(1)

wherein, $R^1$ represents a phenyl group substituted with one or more than one halogen atom or a phenyl group substituted with a trifluoromethyl group; $R^2$ and $R^3$ each represents a fluorine atom or an alkyl group, or may be coupled together to form a lower alkylene group; and $R^4$ represents an alkyl group, or salt thereof; and a medicament comprising the derivative or salt as an effective ingredient.

In another aspect of the present invention, there is also provided a pharmaceutical composition comprising an azole derivative represented by the above-described formula (1) or salt thereof; and a pharmaceutically acceptable carrier.

In a further aspect of the present invention, there is also provided use, as a medicament, of an azole derivative represented by the above-described formula (1) or salt thereof.

In a still further aspect of the present invention, there is also provided a method for treating infectious diseases, which comprises administering an azole derivative represented by the above-described formula (1) or salt thereof.

Since the azole derivatives or salts thereof according to the present invention exhibit excellent antimycotic action and at the same time, good solubility in an aqueous solvent, they are suited for an intravenously administrable preparation and orally administrable preparation.

DETAILED DESCRIPTION OF THE PREFERRED EMBODIMENTS

In the azole derivative (1) of the present invention, examples of the halogen atom which is substituted for the phenyl group of $R^1$ include fluorine, chlorine, bromine and iodine atoms, with fluorine atom being particularly preferred. As $R^1$, a difluorophenyl or (trifluoromethyl)phenyl, particularly 2,4-difluorophenyl or 4-(trifluoromethyl)phenyl group is desired.

As the alkyl group of $R^2$ or $R^3$, linear or branched $C_{1-5}$ alkyl groups are preferred and specific examples include methyl, ethyl, n-propyl, i-propyl, n-butyl, i-butyl, sec-butyl, tert-butyl and n-pentyl groups. As $R^2$ and $R^3$, fluorine atom and methyl group are preferred. It is more preferred that $R^2$ and $R^3$ represent the same group.

Preferred examples of the alkylene group formed through coupling of $R^2$ and $R^3$ include $C_{2-5}$ alkylene groups and specific examples include ethylene, trimethylene, tetramethylene and pentamethylene, with an ethylene group (—$CH_2CH_2$—) being particularly preferred. When $R^2$ and $R^3$ are coupled into the alkylene group, they form a saturated cyclic hydrocarbon with the adjacent carbon atom.

Preferred examples of the alkyl group represented by $R^4$ include linear, branched or cyclic $C_{1-10}$ alkyl groups, with linear or branched $C_{1-4}$ alkyl or $C_{3-6}$ cycloalkyl groups being particularly preferred. Specific examples include methyl, ethyl, n-propyl, i-propyl, n-butyl, i-butyl, sec-butyl, tert-butyl, cyclopropyl, cyclobutyl, cyclopentyl and cyclohexyl groups, of which methyl, ethyl and cyclopropyl groups are most preferred.

Any pharmaceutically acceptable salt can be used as the salt of the azole derivative (1) of the present invention. Examples include hydrochloride, nitrate, hydrobromide, p-toluenesulfonate, methanesulfonate, fumarate, succinate and lactate.

The azole derivatives (1) of the present invention include those containing an asymmetric carbon atom so that they can exist as optically active substances. The racemic mixtures and optically active substances are all embraced in them. In addition, their solvates such as hydrates are also embraced in them.

The azole derivatives (1) or salts thereof can each be prepared, for example, in accordance with the following reaction scheme.

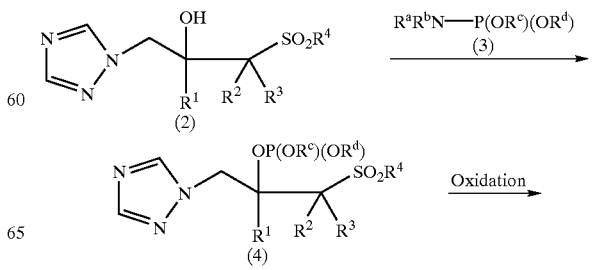

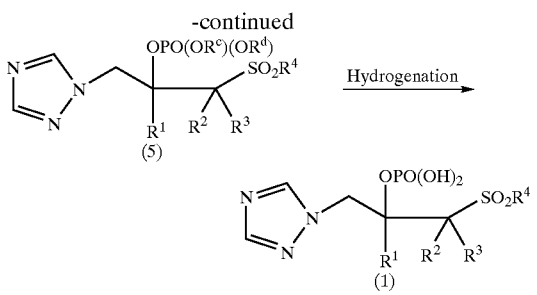

wherein, $R^a$ and $R^b$ each independently represents a $C_{1-6}$ alkyl group or a phenyl group which may contain a substituent, or $R^a$ and $R^b$ may form, together with a nitrogen atom bonded thereto, a ring such as morpholine ring, $R^c$ and $R^d$ each independently represents a hydroxy protecting group and $R^1$ to $R^4$ have the same meanings as described above.

Described specifically, the target azole derivative (1) can be prepared by reacting Compound (2) with Compound (3) to obtain Compound (4), oxidizing the resulting Compound (4) into Compound (5) and then, hydrogenating the resulting Compound (5).

This preparation process will next be described more specifically.

Compound (2) serving as a raw material is available, for example, by the process described in Japanese Patent Application Laid-Open No. Hei 3-223266, 9-227531, 11-240871 and 11-279160.

First, Compound (4) is prepared by reacting Compound (2) with Compound (3). Examples of the hydroxy protecting group of $R^c$ or $R^d$ of Compound (3) used here include a benzyl group which may be substituted with a halogen atom and $C_{1-6}$ alkyl groups such as t-butyl. The benzyl group can be removed later by catalytic hydrogenation, while the $C_{1-6}$ alkyl group can be removed under hydrolysis conditions. As a preferred example of Compound (3), dibenzyl diisopropylphosphoramidite ($R^a$, $R^b$=isopropyl, $R^c$, $R^d$=benzyl) commercially available from Sigma-Aldrich can be mentioned.

In the reaction between Compound (2) and Compound (3), a reaction solvent which does not adversely affect the reaction such as methylene chloride, chloroform or ethyl acetate can be used, with methylene chloride being particularly preferred.

Examples of the additive include 1H-tetrazole, 4-dimethylaminopyridine, tetrazole hydrobromide, 5-methyltetrazole hydrobromide and pyridinium hydrobromide.

The reaction is desirably conducted at room temperature or greater, of which the room temperature is more desired.

Compound (4) can be converted into Compound (5) by oxidation. Examples of the oxidizing agent usable here include m-chloroperbenzoic acid, aqueous hydrogen peroxide, peracetic acid, potassium permanganate and oxone. As the reaction solvent, a solvent not adversely affecting the reaction such as methylene chloride, chloroform or ethyl acetate is preferred, with methylene chloride being particularly preferred. The reaction is preferably conducted at temperature less than room temperature, with 0° C. being more preferred.

The hydroxy-protected phosphate ester represented by the formula (5) is then hydrogenated in the presence of a catalyst, whereby the compound represented by the formula (1) can be obtained.

Examples of the catalyst in the reaction solvent include palladium carbon and Pearlsman's catalyst.

The catalyst is used in an amount of 0.01 to 10 times the weight of Compound (5), with 0.1 to 1 time being preferred.

As a reaction solvent, those inert to the starting compound (5) are preferred. Examples include alcohols such as methanol, ethanol, n-propanol, isopropanol, n-butanol, tert-butanol, ethylene glycol, propylene glycol, glycerin and methyl cellosolve; ethers such as tetrahydrofuran, dioxane and dimethoxyethane; amides such as N,N-dimethylformamide and N,N-dimethylacetamide; and dimethyl sulfoxide. They may be used either singly or in combination as a mixed solvent. The solvent particularly preferred among them is methanol.

The reaction temperature ranges from 0 to 100° C., preferably 10 to 50° C., reaction time ranges from 1 to 200 hours, preferably 5 to 48 hours, and reaction pressure ranges from atmospheric pressure to 300 psi, preferably 40 to 30 psi.

After completion of the reaction, the catalyst is removed and the solvent is distilled off, and the residue is purified by recrystallization, chromatography or the like means, whereby the invention compound represented by the formula (1) can be isolated.

The invention compound of the formula (1) can be converted into its pharmaceutically acceptable salt, for example, inorganic salt with hydrochloric acid, sulfuric acid, nitric acid, phosphoric acid or hydrobromic acid; or organic salt with fumaric acid, maleic acid, acetic acid, malic acid, tartaric acid, citric acid, methanesulfonic acid or p-toluenesulfonic acid.

Since the invention compound (1) or salt thereof thus obtained exhibits excellent antimycotic action, has high safety, and exhibits high solubility in an aqueous solvent enough for permitting formulation into an intravenously administrable preparation or orally administrable preparation, it is useful as a medicament for the prevention or treatment of various mycotic infectious diseases of animals including human being.

The invention compound can be formulated into pharmaceutical compositions, particularly antimycotics, of various dosage forms such as tablets, granules, powders, capsules, suspensions, injections, suppositories, liquid preparations, creams and ointments in a conventional manner by adding a pharmaceutically acceptable carrier. A solid preparation is preferably prepared by adding, to the invention compound, an excipient and optionally, a binder, a disintegrator, an extender, a coating agent or sugar coating agent and then forming the resulting mixture into tablets, granules, capsules or the like in a conventional manner. An injection is preferably prepared by dissolving, dispersing or emulsifying the invention compound in an aqueous carrier such as distilled water for injection in advance; or pulverizing the invention compound into powder and reconstituting it as an injection upon use. Examples of the administration method of the injection include intravenous administration, arterial administration, intraperitoneal administration, subcutaneous administration and intravenous infusion. A dermatologic preparation for external use is preferably prepared by adding, to the invention compound, an oil base or emulsion base and then forming the resulting mixture into a suppository, liquid preparation, cream or ointment in a conventional manner.

The invention compound is administered at a daily dosage of 1 mg to 10 g, preferably 3 mg to 50 mg per adult in one to several portions.

EXAMPLES

The present invention will hereinafter be described more specifically by the following examples. It should however be borne in mind that the present invention is not limited to or by them.

Referential Example 1

Synthesis of Dibenzyl [1-(2,4-difluorophenyl)-2-(ethylsulfonyl)-2,2-difluoro-1-(1H-1,2,4-triazol-1-ylmethyl)ethyl]phosphonate (Optical Active Substance)

A solution of (−)-2-(2,4-difluorophenyl)-1-(ethylsulfonyl)-1,1-difluoro-3-(1H-1,2,4-triazol-1-yl)-2-propanol (1.0 g, 3.27 mmol), 1H-tetrazole (0.69 g, 9.80 mmol) and dibenzyl diisopropylphosphoramide (2.44 g, 6.54 mmol) in dichloromethane (50 ml) was stirred at room temperature for 3 hours under a nitrogen gas atmosphere. After ice cooling, m-chloroperbenzoic acid (0.97 g, 3.92 mmol) was added in portions, followed by stirring at room temperature for 1 hour. An aqueous solution (10%) of sodium thiosulfate and a saturated aqueous solution of sodium bicarbonate were added to the reaction mixture for extraction. The organic layer thus obtained was washed with water, dried over magnesium sulfate, and distilled under reduced pressure. The residue was purified by chromatography on a silica gel column using dichloromethane, whereby the title compound (1.90 g, yield: 92.7%) was obtained.

$^1$H-NMR (CDCl$_3$)δ: 1.29(t,3H,J=8 Hz), 2.96(q,2H,J=8 Hz), 4.9–5.0(m,2H), 5.16(d,2H,J=7 Hz), 5.50(d,1H,J$_{AB}$=15 Hz), 5.92(d,1H,J$_{AB}$=15 Hz), 6.6–7.1 (m,2H), 7.1–7.7(m, 1H), 7.36(s,10H), 7.69(s,1H), 8.54(s,1H).

Referential Example 2

Synthesis of Dibenzyl [1-(2,4-difluorophenyl)-2,2-difluoro-2-(methylsulfonyl)-1-(1H-1,2,4-triazol-1-ylmethyl)ethyl]phosphonate (Optical Active Substance)

In a similar manner to Referential Example 1 except for the use of (−)-2-(2,4-difluorophenyl)-1,1-difluoro-1-(methylsulfonyl)-3-(1H-1,2,4-triazol-1-yl)-2-propanol, the title compound was obtained (yield: 78.9%).

$^1$H-NMR(CDCl$_3$) δ: 2.7–2.8(m,3H), 4.9–5.0(m,2H), 5.16 (d,2H,J=8 Hz), 5.50(d,1H,J$_{AB}$=15 Hz), 5.89(d,1H,J$_{AB}$=15 Hz), 6.6–7.1(m,2H), 7.1–7.7(m,1H), 7.36(s,10H), 7.68(s,1H),8.52(s,1H).

Referential Example 3

Synthesis of Dibenzyl [1-(1-methylsulfonyl) cyclopropyl)-2-(1H-1,2,4-triazol-1-yl)-1-(4-(trifluoromethyl)phenyl)ethyl]phosphonate (Optical Active Substance)

A solution of (+)-1-(1-(methylsulfonyl)cyclopropyl)-2-(1H-1,2,4-triazol-1-yl)-1-(4-(trifluoromethyl)phenyl)-1-ethanol (1.0 g, 2.67 mmol), 4-dimethylaminopyridine (0.55 g, 4.53 mmol), 1H-tetrazole (0.56 g, 8.00 mmol) and dibenzyl diisopropylphosphoramidite (1.99 g, 5.33 mmol) in dichloromethane (50 ml) was stirred under reflux for 2 hours in a nitrogen gas atmosphere, followed by stirring at room temperature for further 2 hours. The reaction mixture was washed successively with diluted hydrochloric acid, a saturated aqueous solution of sodium bicarbonate and water, dried over magnesium sulfate and distilled under reduced pressure to remove the solvent. The residue thus obtained was purified by chromatography on a silica gel column using chloroform, whereby a colorless oil (1.46 g) was obtained. The resulting oil was dissolved in dichloromethane (50 ml). A solution of m-chloroperbenzoic acid (0.66 g, 2.67 mmol) in dichloromethane (20 ml) was added to the resulting solution under ice cooling, while maintaining its temperature at 0° C. or less. After heating to room temperature over 20 minutes, the reaction mixture was added with an aqueous solution (10%) of sodium thiosulfate and a saturated aqueous solution of sodium bicarbonate for extraction. The resulting organic layer was washed with water, dried over magnesium sulfate and distilled under reduced pressure to remove the solvent. The residue thus obtained was purified by chromatography on a silica gel column using chloroform, whereby the title compound (1.24 g, yield: 72.1%) was obtained.

$^1$H-NMR(CDCl$_3$) δ: 0.1–0.5(m,1H), 0.7–1.1(m,1H), 1.1–1.6(m,2H), 1.85(s,3H), 4.5–4.7(m,2H), 5.0–5.3(m,2H), 5.75(d,1H,J$_{AB}$=15 Hz), 6.01(d,1H,J$_{AB}$=15 Hz), 7.33(s,10H), 7.59(d,2H,J=9 Hz), 7.79(d, 2H,J=9 Hz), 7.93(s,1H), 8.51(s, 1H).

Example 1

Synthesis of (+)-1-(2,4-difluorophenyl)-2-(ethylsulfonyl)-2,2-difluoro-1-(1H-1,2,4-triazole-1-ylmethyl)ethyl Dihydrogen Phosphate A Pearlman's catalyst (400 mg) was added to a solution of dibenzyl [1-(2,4-difluorophenyl)-2-(ethylsulfonyl)-2,2-difluoro-1-(1H-1,2,4-triazol-1-ylmethyl)ethyl]phosphonate (optical active substance) (1.86 g, 2.97 mmol) in methanol (40 ml), followed by stirring at room temperature for 16 hours at 59 psi to hydrogenate the compound. After removal of the catalyst by filtration, the residue was washed with methanol and the washing was concentrated. The crystals thus precipitated were recrystallized from methanol, whereby the title compound (490 mg, yield: 37.0%) was obtained.

Melting point: 212 to 214° C.; MS (FAB): 448 (M+H) $^1$H-NMR (DMSO-d$_6$) δ: 6: 1.25(t,3H,J=7.3 Hz), 3.30–3.45 (m,2H), 5.33(d,1H,J$_{AB}$=15 Hz), 5.85(d,1H,J$_{AB}$=15 Hz), 7.04–7.09(m,1H), 7.16–7.23(m,1H), 7.63–7.69(m,1H), 7.78 (s,1H), 8.65(s,1H), 10–12(br.,2H); $^{19}$F-NMR(DMSO-d$_6$) δ: −33.50 to −33.41(m,1F), −30.18(dd,1F,J=243 Hz,48 Hz), −29.59(dd,1F,J=242 Hz,17 Hz),−25.02 to −24.76(m,1F). $^{31}$P-NMR(DMSO-d$_6$) δ: −6.79. IR(KBr): 1617, 1501, 1345, 1156cm$^{-1}$; [α]$_D^{20}$=+6.0° (c=0.1,H$_2$O).

Example 2

Synthesis of (+)-1-(2,4-difluorophenyl)-2,2-difluoro-2-(methylsulfonyl)-1-(1H-1,2,4-triazol-1-ylmethyl)ethyl Dihydrogen Phosphate In a similar manner to Example 1 except for the use of dibenzyl [1-(2,4-difluorophenyl)-2,2-difluoro-2-(methylsulfonyl)-1-(1H-1,2,4-triazol-1-ylmethyl)ethyl] phosphonate (optical active substance), the title compound was obtained (yield: 48.8%).

Melting point: 216 to 218° C.; MS(FAB): 434(M+H). $^1$H-NMR(DMSO-d$_6$) δ: 3.22(s,3H), 5.33(d,1H,J$_{AB}$=15 Hz), 5.86(d,1H,J$_{AB}$=15 Hz), 7.04–7.10(m,1H), 7.17–7.24(m,1H), 7.62–7.69(m,1H), 7.78(s,1H), 8.65(s,1H). $^{19}$F-NMR (DMSO-d$_6$) δ: −33.49 to −33.39(m,1F), −32.64(dd,1F,J=243 Hz,J=55 Hz), −30.01(dd,1F,J=243 Hz,J=11 Hz), −25.09 to −24.88(m,1F). $^{31}$P-NMR(DMSO-d$_6$) δ: −6.83 (S). IR(KBr): 1600, 1500, 1350, 1122cm$^{-1}$ [α]$_D^{25}$=+5.00° (c=0.1,H$_2$O).

Example 3

Synthesis of (+)-1-(1-(methylsulfonyl)cyclopropyl)-2-(1H-1,2,4-triazol-1-yl)-1-(4-(trifluromethyl) phenyl)ethyl Dihydrogen Phosphate In a similar manner to Example 1 except for the use of dibenzyl [1-(1-(methylsulfonyl)cyclopropyl)-2-(1H-1,2,4- triazol-1-yl)-1-(4-(trifluoromethyl)phenyl)ethyl]
phosphonate (optical active substance), the title compound
was obtained (yield: 17.7%).

Melting point: 234 to 236° C., MS(FAB): 456(M+H).
$^1$H-NMR(DMSO-$d_6$) δ: 0.3–0.4(m,1H), 1.1–1.2(m,1H), 1.2–1.3(m,1H), 1.5–1.6(m,1H), 2.05(s,3H), 5.49(d,1H,$J_{AB}$=15 Hz), 5.88(d,1H,$J_{AB}$=15 Hz), 7.80(d,2H,J=8 Hz), 7.91(d,2H, J=8 Hz), 8.01(s,1H), 8.57(s,1H). $^{19}$F-NMR(DMSO-$d_6$) δ: 14.13(s). $^{31}$P-NMR(DMSO-$d_6$) δ: –5.96(s). IR(KBr): 1335, 1313, 1132, 1072 cm$^{-1}$ $[α]_D^{25}$=+30.0 ° (c=0.1, H$_2$O).

Example 4

In similar manners to the aforementioned Referential Examples and Examples,2-(cyclopropylsulfonyl)-1-(2,4-difluorophenyl)-2,2-difluoro-1-(1H-1,2,4-triazol-1-ylmethyl)ethyl dihydrogen phosphate was obtained.

Example 5

The compound obtained in Example 1 was compared in aqueous solubility with a parent (non-phosphorylated) compound (in the form of a free base). The results are shown in Table 1.

TABLE 1

| Compound | Solubility (mg/mL) |
|---|---|
| Example 1 | 4.80 |
| Parent compound | 0.50 |

Example 6

In vivo Activities against the *Candida albicans* Murine Model

Four-week-old male ICR mice were fasted for 6 hours. The mice were inoculated at 3×10$^6$ cells/mouse of *C. albicans* IFM 40009 into the tail vein. The infection control group and the drug-treated group consisted of 10 and 5 animals, respectively. The compound of Example 1 and the parent compound were dissolved in 20% polyethylene glycol 200. The drug solutions were intravenously administered at the dose of 1 mg/kg once daily for 4 consecutive days after infection. Survival or death of the animals was observed for 14 days after infection. Paired comparison of duration of survival between the infection control and drug-treated groups were analyzed by Log-Rank test. Results are shown in Table 2.

TABLE 2

| Test compound | Average surviving days |
|---|---|
| Example 1 | 14.0*** |
| Parent compound | 14.0*** |
| Infection control | 3.2 |

***P < 0.001 relative to Infection control

What is claimed is:
1. An azole compound represented by the following formula (1):

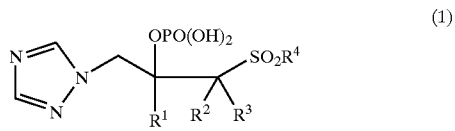

(1)

wherein

R$^1$ represents a phenyl group substituted with one or more than one halogen atom or a phenyl group substituted with a trifluoromethyl group, R$^2$ and R$^3$ each represents a fluorine atom or an alkyl group, or may be coupled together to form a lower alkylene group, provided that when R$^1$ is phenyl substituted with trifluoromethyl, then either R$^2$ or R$^3$ is fluorine, and R$^4$ represents an ethyl group, or a salt thereof.

2. A composition comprising the compound or salt of claim 1 and a pharmaceutically acceptable carrier.

3. The composition of claim 2 in a form suitable for oral administration.

4. The composition of claim 2 in a form suitable for injection or intravenous administration.

5. The composition of claim 2 in a form suitable for external application or for dermatological use.

6. The composition of claim 2 in the form of a tablet, granule, powder, capsule, suspension, injection, suppository, liquid, cream or ointment.

7. A method for treating a mycotic disease comprising administering an effective amount of the compound of claim 1 to a subject in need thereof.

8. The compound of claim 1, wherein R$^1$ is a phenyl substituted with one or more fluorine, chlorine, bromine or iodine atoms.

9. The compound of claim 1, wherein R$^1$ is difluorophenyl.

* * * * *